United States Patent [19]

Ramirez et al.

[11] Patent Number: 6,054,425
[45] Date of Patent: Apr. 25, 2000

[54] CLEANSING BAR WITH HIGH LEVELS OF EMOLLIENTS AND PARTICULATE SILICA

[75] Inventors: Jose E. Ramirez, Trumbull; Mohan Vishnupad, Monroe, both of Conn.

[73] Assignee: Imaginative Research Associates, Inc., Milford, Conn.

[21] Appl. No.: 08/650,235

[22] Filed: May 20, 1996

[51] Int. Cl.[7] .......................... C11D 17/00; C11D 11/02; A61K 7/50
[52] U.S. Cl. .......................... 510/447; 510/450; 510/442; 510/152; 510/155; 510/156
[58] Field of Search ........................ 510/450, 447, 510/442, 152, 155, 156; 134/40

[56] References Cited

U.S. PATENT DOCUMENTS

| | | |
|---|---|---|
| 3,903,008 | 9/1975 | Deweever et al. . |
| 4,100,097 | 7/1978 | O'Roark ................ 252/145 |
| 4,405,492 | 9/1983 | Nyquist et al. ........... 252/370 |
| 4,574,053 | 3/1986 | Kinsman et al. . |
| 4,673,525 | 6/1987 | Small et al. . |
| 4,673,528 | 6/1987 | Artz et al. ............ 252/188.25 |
| 4,695,395 | 9/1987 | Caswell et al. .......... 252/121 |
| 4,719,030 | 1/1988 | Williams et al. . |
| 4,808,322 | 2/1989 | McLaughlin ............ 252/121 |
| 4,812,253 | 3/1989 | Small et al. ............ 252/132 |
| 4,839,080 | 6/1989 | Jungermann et al. . |
| 4,851,147 | 7/1989 | Esposito et al. .......... 252/138 |
| 4,941,990 | 7/1990 | McLaughlin ............ 252/121 |
| 5,204,014 | 4/1993 | Redd et al. ............. 252/117 |
| 5,227,086 | 7/1993 | Kacher et al. ........... 252/112 |
| 5,254,334 | 10/1993 | Ramirez et al. . |
| 5,342,535 | 8/1994 | Ramirez et al. .......... 252/135 |
| 5,409,706 | 4/1995 | Ramirez et al. .......... 424/401 |
| 5,496,488 | 3/1996 | Kacher et al. . |
| 5,547,602 | 8/1996 | Schuker . |
| 5,607,980 | 3/1997 | McAtee et al. ........... 514/476 |
| 5,661,189 | 8/1997 | Grieveson et al. ....... 514/784 |
| 5,770,556 | 6/1998 | Farrell et al. . |
| 5,783,536 | 7/1998 | Farrell et al. . |

FOREIGN PATENT DOCUMENTS

| | | |
|---|---|---|
| 2084050 | 5/1993 | Canada . |
| 0194126 | 9/1986 | European Pat. Off. . |
| 1708827 | 1/1992 | U.S.S.R. . |
| 783223 | 9/1957 | United Kingdom . |
| WO 96/29983 | 10/1996 | WIPO . |
| WO 97/36985 | 10/1997 | WIPO . |
| WO 97/49381 | 12/1997 | WIPO . |

OTHER PUBLICATIONS

Milwidsky, Ben., Syndet Bars, Happi vol.22, No. 5, May, 1985, pp. 58–70.

CAB–O–SIL Fumed Silica: Properties and Functions, Cabot Corporation, 1990 no month available.

*Primary Examiner*—Necholus Ogden
*Attorney, Agent, or Firm*—Dilworth & Barrese

[57] ABSTRACT

Cleansing bars are formed from compositions containing an oil phase, particulate silica and a cleansing agent. The particulate silica is present in an amount to provide sufficient hardness to the composition to facilitate processing into a bar while maintaining good foaming despite a high oil content.

6 Claims, No Drawings

CLEANSING BAR WITH HIGH LEVELS OF EMOLLIENTS AND PARTICULATE SILICA

FIELD OF THE INVENTION

This disclosure relates generally to personal cleansing bars with lathering detergents and/or soaps. The bars have a high oil and/or wax content in combination with lathering additives and particulate silica to give the bars a desirable consistency.

DESCRIPTION OF THE RELATED ART

Personal cleansing with mild surface-active cleansing bar preparations has become a focus of great interest. The processability and smear properties of such bars have become a focus of even greater interest.

The fabrication of relatively pure "soap" bars is a well-worked-out engineering procedure involving milling, plodding and molding. Coco/tallow soap becomes quite plastic when warmed and can be easily plodded and molded under relatively low pressures. However, bars made with certain mild surfactants are very difficult to fabricate. The problems of formulating such bars are not limited to the performance characteristics of the finished bars. Thus, problems associated with mild synthetic detergent bars include bar processability, firmness, smear and mildness. For example, most synthetic detergents and detergent-filler combinations do not become plastic and the machinery for fabrication must be specially designed. See e.g., U.S. Pat. No. 2,678,921.

Ideal processing should be fast and problem free in terms of milling, plodding and molding toilet bar formation. Most mild bar processings fall short in this respect.

Major drawbacks of most synthetic surfactant toilet bar formulations are harshness, poor lather, poor smear, and poor processsability due to stickiness. It will be appreciated that processability, firmness, smear, mildness, lather, and rinsability make surfactant selection for mild personal cleansing bars a delicate balancing act. Thus, rather stringent requirements for formulating mild personal cleansing bars limit the choice of surfactants, and final formulations represent some degree of compromise. Mildness is often obtained at the expense of processability, effective cleansing, lathering, or rinsing, or vice versa. Processability is often obtained at the expense of smear.

A superior processable mild personal cleansing bar formulation with good mildness, good smear, good lather potential and good rinsability is difficult to formulate, but would be highly desirable.

SUMMARY OF THE INVENTION

It has now been discovered that particulate silica in certain ratios with oils, waxes, petrolatum, esters in combination with detergent and/or soap additives can be formulated into cleansing bars of good hardness and acceptable processing characteristics. A unique feature of such compositions is that the high levels of oils, waxes, petrolatum, esters, etc. provide functional benefits to skin by providing good foam without defatting the skin. Silica gives the bar the necessary properties for commercial fabrication.

A novel finding of these compositions is the effect of particulate silica having a high surface area on detergents from the groups consisting of sodium acyl isethionate, sodium alpha olefin sulfonates, disodium alkyl sulfosuccinate, soap base, tallow and coco sodium salts, and mixtures thereof, which produces a hard processable cleansing bar. Silica in the presence of these detergents, soaps and blends thereof, hardens the bars significantly. The hardening effect desirable for processing is observed at silica contents of a minimum of 1 part silica to 10 parts of oil on a w/w basis, varying according to the particular oils and waxes employed.

Particularly useful embodiments of the present cleansing bar compositions contain: an oily phase consisting of either mineral or vegetable oils with or without the addition of waxes; amorphous silica; and soap, detergent or a mixture thereof. The composition is capable of foaming when combined with water during use. The present compositions provide formulations of a flowable phase of oils or oils and waxes and silica which, upon combination with soap and/or detergents can be processed and stamped into a cleansing bar.

DETAILED DESCRIPTION OF THE PREFERRED EMBODIMENTS

This disclosure relates generally to formulations of cleansing bars having high oil content and containing levels of a suitable hardening agent or agents in combination with soap and/or detergents and additives that give the bars a desirable consistency. More particularly, this disclosure is concerned with the discovery that cleansing bars with soap and/or detergents and high levels of oils can be formulated properly and fabricated using well-established equipment and procedures. In contrast, most synthetic detergents and detergent-filler combinations that are presently available do not become plastic and modifications have to be made to the manufacturing equipment and fatty acids and soap-like ingredients have to be added for suitable manufacturing.

The use of oils and other hydrophobic materials like petrolatum, paraffin and waxes is well known in the fabrication of bars. However, because of their foam suppressing and softening properties, the use of oils and waxes is limited to low levels in cleansing bars. Furthermore, their use in synthetic detergent bars softens the product, making it very difficult to prepare a suitable commercial bar. A novel finding of the compositions described herein is that silica when used in certain ratios with oils, allows the preparation of cleansing bars that can be processed using established manufacturing methods while aiding with the foaming characteristics of the bars.

The first component of the compositions described herein is an oil phase which contains oils and, optionally, waxes. The oils can be mineral oils which are a purified mixture of liquid hydrocarbons obtained from petroleum. Normally, mineral oils are a mixture of oils of the methane series having the general formula $C_nH_{2n+2}$. Alternatively, the oils can be of vegetable origin, that is extracted from the seeds, fruits or leaves of plants and generally considered to be mixtures of mixed glycerides (e.g., sesame, avocado, olive, cottonseed, etc.). Mixtures of vegetable and mineral oils can also be used in the oil phase. The oils can be modified by the addition of paraffinic and microcrystalline waxes. A particularly useful oil phase is petrolatum. Petrolatum is a combination of mineral oils and wax which forms a white to faintly yellow unctuous mass of well recognized pharmaceutical properties. The preferred white petrolatum USP has a density of from about 0.82 to about 0.865, a melting point of from about 38° to 54° C. and a refractive index of from about 1.460 to 1.474.

In particularly useful ebodiments, the oil phase constitutes from about 15 to about 45 percent by weight of the final composition. Preferably, the oil phase is from about 20 to about 40 weight percent of the final composition.

The second component of the present compositions is an effective amount of silica. Silica gives the oil phase an appropriate degree of solid characteristic so that the resulting mixture can be processed with soaps, detergents or mixtures thereof. Any particulate silica having a surface area greater than about 75 m$^2$/g is suitable. Preferably, the particulate silicon is amorphous and has a surface area of greater than 100 m$^2$/gm. A particularly useful amorphous silica is fumed silica. Fumed silica is fumed silicon oxide, SiO$_2$, a material which is produced by the hydrolysis of silicon tetrachloride vapor in a flame of hydrogen and oxygen. In the combustion process, molten spheres of silica are formed with extremely small particle size and enormous surface area. The resulting fumed silica is a fluffy white powder of very low bulk density, from 2.5 to 5 lbs./ft$^3$ and a surface area from 10 to 380 m$^2$/gm. Other silicas having the desired surface area are also suitable; such as, for example precipitated silicas or silica fume.

The particulate silica should be present in the composition in an amount sufficient to harden the composition. The hardness of the composition is conveniently ascertained by measuring penetration value as described more fully hereinafter. The ratio of oil phase to silica is preferably greater than about 2:1 more preferably in the range of about 4:1 to about 10:1. In particularly useful embodiments, the effective amount of particulate silica will range from about 3 percent by weight of the final composition to about 20 percent by weight of the final composition. Preferably, from about 5 to about 15 weight percent silica is present.

The third component of the present composition is a cleansing agent, e.g., a soap, a detergent or a mixture thereof. In a mixture with the other components described above, a composition is produced that can be processed and stamped into a cleansing bar and when combined with water exhibits foaming behavior. A particularly useful soap base suitable for personal care is a blend of tallow and coco sodium salts (80/20). Representative classes of detergents which have been found to be useful are the sodium acyl isethionates, the sodium alpha olefin sulfonates and disodium alkyl sulfosuccinates. However, this disclosure is not limited to these detergents.

The amount of cleansing agent included in the composition will vary depending on the exact detergent chosen, the identity of other components employed, and the desired physical and performance characteristics to be achieved. Normally, however, the amount of cleansing agent in particularly useful embodiments will range from about 25 to about 85 percent by weight of the final composition. Preferably, the cleansing agent is present in an amount from about 40 to about 75 percent by weight of the final composition.

The detergent chosen should be mild to the skin and relatively unaffected by ions which might be present in hard water. An unusual finding in connection with the compositions of this disclosure is that when adding silica to oils or oils and waxes (preferably molten), and processing the resulting composition through a blade blender and a screw mixer, the resulting mass can be compacted into a solid that has similar hardness characteristics as compacted soaps, detergents or mixtures thereof. This allows the blend of oils or oils and waxes and silica to be added to the soap, detergent or mixtures thereof without the resulting softening characteristics of adding oils by themselves.

In addition to the foregoing components, foam boosters may be incorporated into the present compositions. Suitable foam enhancers include potassium polymetaphosphate, sodium lauryl sulfoacetate, sodium lauryl sulfate, sodium lauryl sarcosinate, acyl glutamate and amides. These materials will enhance the foam produced when the present compositions are exposed to water during use.

The compositions may also contain conventional additives such as fragrance, color, fillers, preservatives, etc. Additionally, active ingredients may be incorporated in the present compositions. Such active ingredients include, but are not limited to deodorants, medicaments such as, for example coal-tar, benzoyl peroxide, vitamin A and vitamin E, and antibacterial ingredients such as, for example, triclosan, PVP-iodine and salicylic acid. The amount of active ingredient included in the present compositions should be an "effective amount" by which it is meant an amount sufficient to achieve a desired effect. The precise amount that is effective will depend upon the particular active ingredient and the desired effect to be achieved. Normally, an effective amount will be from about 0.001 to about 10 weight percent, more preferably from about 0.01 to about 5.0 weight percent.

The order of addition of the ingredients of the present compositions is not critical. The compositions described herein are preferably prepared by first mixing the ingredients of the oil phase. Silica is then added to the oil phase. Heating and vigorous mixing may be used to aid in providing a homogenous oil/silica composition. Next, the cleansing agent is added to and mixed with the oil/silica mixture. At this point, the composition can be pelletized, if desired. Finally, any additives (fragrance, filler, active ingredient, etc.) are added to the composition. Once prepared, the composition can be formed into a bar using known techniques. One such technique is described, for example, in U.S. Pat. No. 4,812,253, the disclosure of which is incorporated herein by this reference.

EXAMPLES 1–4

Examples 1–4 present formulations of the compacted mass that is produced when fumed silica and petroleum jelly are mixed and properly processed.

The compositions of Examples 1 to 4 show the effect that changing the ratios of silica to petrolatum has on the consistency of the compacted mass. Comparative example A has been included to show the consistency of pure petrolatum. The petroleum jelly employed in the Examples was designated White Petrolatum USP, G1951, and is commercially available from Witco, Greenwich, Conn. The silica used in the Examples presented herein is a fumed silica sold under the trademark CAB-O-SIL, available from Cabot Corp., Tuscola, Ill. The results are presented in Table I.

TABLE I

| Example No. | A | 1 | 2 | 3 | 4 |
| --- | --- | --- | --- | --- | --- |
| Petroleum Jelly USP | 100.0 | 83.3 | 79.4 | 74.6 | 66.6 |
| Fumed Silica | 100.00 | 16.7 | 20.6 | 25.4 | 33.3 |
| R = Si/PJ | 0.0 | 0.2 | 0.26 | 0.34 | 0.5 |
| Penetration Value (mm × 10) | 260.0 | 80.0 | 48.0 | 28.0 | 15.0 |

The consistency of the resulting paste or solid is tested using a Penetrometer (Universal Penetrometer, ASTM, (Precision 73510), Catalog No. 33541, Macalaster Bicknell Company of Connecticut, Inc., New Haven, Conn.) which was equipped with a 300 g cone. The amount of penetration of the cone into the sample was displayed by, and read off, the penetrometer in units of mm×10. A lower penetration value indicates a harder mass. The samples were compacted by adding 20 g of mixture to a die punch. The pasty or powdery mixture was then compressed to form discs 1½" wide by ⅝" high. Preferably, the compositions of this invention have penetration values of less than 50 mm×10 and ratios of silica to oil phase greater than 0.1.

EXAMPLES 5–16

Examples 5 to 16 present the hardness of the compacted mass that is produced when fumed silica, petroleum jelly and soap are mixed and properly processed. The consistency of the resulting paste or solid is tested as previously described, that is by using a Penetrometer and measuring the hardness of the resulting 20 g disc. Comparative examples B, C and D have been included to show the consistency of the commercial soap base with petrolatum and no fumed silica. The results are present in Table II.

TABLE II

| Example No. | B | 5 | 6 | 7 | 8 |
| --- | --- | --- | --- | --- | --- |
| Petroleum Jelly USP | 20.0 | 20.0 | 20.0 | 20.0 | 20.0 |
| Fumed Silica | 0.0 | 4.0 | 5.0 | 6.67 | 10.0 |
| Soap Base* | 80.0 | 76.0 | 75.0 | 73.33 | 70.0 |
| R = Si/PJ | 0.0 | 0.2 | 0.25 | 0.33 | 0.5 |
| Penetration Value (mm × 10) | 80.0 | 35.0 | 28.0 | 25.0 | 15.0 |

| Example No. | C | 9 | 10 | 11 | 12 |
| --- | --- | --- | --- | --- | --- |
| Petroleum Jelly USP | 30.0 | 30.0 | 30.0 | 30.0 | 30.0 |
| Fumed Silica | 0.0 | 6.0 | 7.5 | 10.0 | 15.0 |
| Soap Base* | 76.0 | 64.0 | 62.5 | 60.0 | 55.0 |
| R = Si/PJ | 0.0 | 0.2 | 0.25 | 0.33 | 0.5 |
| Penetration Value (mm × 10) | 135.0 | 58.0 | 45.0 | 28.0 | 15.0 |

| Example No. | D | 13 | 14 | 15 | 16 |
| --- | --- | --- | --- | --- | --- |
| Petroleum Jelly USP | 40.0 | 40.0 | 40.0 | 40.0 | 40.0 |
| Fumed Silica | 0.0 | 8.0 | 10.0 | 13.3 | 20.0 |
| Soap Base* | 60.0 | 52.0 | 50.0 | 46.7 | 40.0 |
| R = Si/PJ | 0.0 | 0.2 | 0.25 | 0.33 | 0.5 |
| Penetration Value (mm × 10) | 270.0 | 65.0 | 50.0 | 28.0 | 15.0 |

*Commercial soap base composition containing:
Sodium Tallowate 68%
Sodium Cocoate 17.0%
Water 12.5
Glycerin 1.0
Pentasodium Pentetate <1.0
Tetrasodium etidronate <1.0

The resulting mixtures required at least 1 part of fumed silica for 10 parts of petroleum jelly for the bars with the lower levels of petroleum jelly (20%) to have a penetration of approximately 50 mm×10. Higher levels of petroleum jelly (40%) require 1 part of fumed silica to 4 parts of petroleum jelly to the hardness of the bars to values of 50 mm×10. It will be pointed out that the hardness of the soap mass processed without fumed silica and without petroleum jelly is 15 mm×10. This value is approached by all the blends of petroleum jelly, silica and soap, once the ratio of fumed silica to petroleum jelly has a value of 0.5, or higher.

EXAMPLES 17–28

Examples 17–28, present the penetration values of the compacted mass that is produced when fumed silica, petroleum jelly and a commercial blend of syndet and soap are mixed and properly processed. The consistency of the paste or solid is tested as previously described. Comparative examples E, F & G have been included to show the consistency of the commercial soap/syndet base with petrolatum and no fumed silica.

TABLE III

| Example No. | E | 17 | 18 | 19 | 20 |
| --- | --- | --- | --- | --- | --- |
| Petroleum Jelly USP | 20.0 | 20.0 | 20.0 | 20.0 | 20.0 |
| Fumed Silica | 0.0 | 4.0 | 5.0 | 6.67 | 10.0 |
| Soap/Syndet Base** | 80.0 | 76.0 | 75.0 | 73.33 | 70.0 |
| R = Si/PJ | 0.0 | 0.2 | 0.25 | 0.33 | 0.5 |
| Penetration Value (mm × 10) | 90.0 | 35.0 | 30.0 | 23.0 | 15.0 |

| Example No. | F | 21 | 22 | 23 | 24 |
| --- | --- | --- | --- | --- | --- |
| Petroleum Jelly USP | 30.0 | 30.0 | 30.0 | 30.0 | 30.0 |
| Fumed Silica | 0.0 | 6.0 | 7.5 | 10.0 | 15.0 |
| Soap/Syndet Base** | 70.0 | 64.0 | 62.5 | 60.0 | 55.0 |
| R = Si/PJ | 0.0 | 0.2 | 0.25 | 0.33 | 0.5 |
| Penetration Volume (mm × 10) | 115.0 | 51.0 | 42.0 | 27.0 | 15.0 |

| Example No. | G | 25 | 26 | 27 | 28 |
| --- | --- | --- | --- | --- | --- |
| Petroleum Jelly USP | 40.0 | 40.0 | 40.0 | 40.0 | 40.0 |
| Fumed Silica | 0.0 | 8.0 | 10.0 | 13.3 | 20.0 |
| Soap/Syndet Base** | 60.0 | 52.0 | 50.0 | 46.7 | 40.0 |
| R = Si/PJ | 0.0 | 0.2 | 0.25 | 0.33 | 0.5 |
| Penetration Value (mm × 10) | 120.0 | 55.0 | 43.0 | 30.0 | 15.0 |

**Soap/Syndet commercial base, as follows:
Sodium cocoylisethionate 45%
Stearic acid 30.0
Sodium Tallowate 10.0
Water 5.0
Sodium stearate 3.0
Sodium cocoate 2.0
Sodium chloride 2.0
less than 1%
Sodium dodecyl benzene sulfonate, PEG-20, sodium isethionate, titanium dioxide, pentasodium pentetate, tetrasodium etidronate.

The resulting mixtures require at least 1.5 parts of fumed silica for 10 parts of petroleum jelly for bars with the lower levels of petroleum jelly (20%) while the higher levels of petroleum jelly (40%) require 1 part of fumed silica to 4 parts of petroleum jelly to increase hardness of the syndet/soap bars to values less than 50 mm×10. It will be pointed out that the hardness of the syndet/soap mass processed without fumed silica and without petroleum jelly is 15 mm×10. This value is approached by all blends of petroleum jelly, silica and syndet/soap, once the ratios of fumed silica to petroleum jelly has a value of 0.5 or higher.

EXAMPLES 29–40

Examples 29–40 present the hardness of the compacted mass that is produced when fumed silica, petroleum jelly and a commercial blend of syndet are mixed and properly processed. Comparative examples H, I & J have been included to show the consistency of the commercial syndet base with petroleum and no fumed silica.

EXAMPLES 29–40

TABLE IV

| Example No. | H | 29 | 30 | 31 | 32 |
| --- | --- | --- | --- | --- | --- |
| Petroleum Jelly USP | 20.0 | 20.0 | 20.0 | 20.0 | 20.0 |
| Fumed Silica | 0.0 | 4.0 | 5.0 | 6.67 | 10.0 |
| Syndet Base*** | 80.0 | 76.0 | 75.0 | 73.33 | 70.0 |
| R = Si/PJ | 0.0 | 0.2 | 0.25 | 0.33 | 0.5 |

TABLE IV-continued

| Penetration Value (mm × 10) | 125.0 | 50.0 | 40.0 | 27.0 | 15.0 |
|---|---|---|---|---|---|

| Example No. | I | 33 | 34 | 35 | 36 |
|---|---|---|---|---|---|
| Petroleum Jelly USP | 30.0 | 30.0 | 30.0 | 30.0 | 30.0 |
| Fumed Silica | 0.0 | 6.0 | 7.5 | 10.0 | 15.0 |
| Syndet Base*** | 70.0 | 64.0 | 62.5 | 60.0 | 55.0 |
| R = Si/PJ | 0.0 | 0.2 | 0.25 | 0.33 | 0.5 |
| Penetration Value (mm × 10) | 210.0 | 40.0 | 25.0 | 18.0 | 15.0 |

| Example No. | J | 37 | 38 | 39 | 40 |
|---|---|---|---|---|---|
| Petroleum Jelly USP | 40.0 | 40.0 | 40.0 | 40.0 | 40.0 |
| Fumed Silica | 0.0 | 8.0 | 10.0 | 13.3 | 20.0 |
| Syndet Base*** | 60.0 | 52.0 | 50.0 | 46.7 | 40.0 |
| R = Si/PJ | 0.0 | 0.2 | 0.25 | 0.33 | 0.5 |
| Penetration Value (mm × 10) | 250.0 | 80.0 | 55.0 | 30.0 | 15.0 |

***Commercial syndet base
Sodium cocoylisethionate 50%
Stearic acid 33%
Water 10%
Sodium isethionate 5%
Titanium dioxide 1.0
Sodium chloride 1.0

The consistency of the paste or solid is tested as previously described. The resulting mixtures require at least 1 part of fumed silica for 5 parts of petroleum jelly for bars with the lower levels of petroleum jelly (20%) while the higher levels of petroleum jelly (40%) require 1 part of fumed silica to 3.5 parts of petroleum jelly to increase hardness of the syndet bars to values of 50 mm×10. It will be pointed out that the hardness of the syndet mass processed without fumed silica and petroleum jelly is 15 mm×10. This value is approached by all blends of petroleum jelly, silica and syndet, once the ratio of fumed silica to petroleum jelly has a value of 0.5 or higher (that is 1 part of fumed silica to 2 parts of petroleum jelly).

The following are additional specific, non-limiting examples of compositions in accordance with the present invention.

EXAMPLE 41

|  | % | 250 g |
|---|---|---|
| EXAMPLE 41 | | |
| Petroleum Jelly | 40.00 | 100.00 |
| Fumed silica | 8.00 | 20.00 |
| Sodium cocoyl isethionate | 52.00 | 130.00 |

Comments: Penetration = 50; Si/PJ = 0.2; foams well. The sodium cocoyl isetionate used in this and other Examples is available under the designation Tauranol I-78 from Finetex, Inc., Elmwood Park, New Jersey.

| EXAMPLE 42 | | |
|---|---|---|
| Petroleum Jelly | 40.00 | 100.00 |
| Fumed Silica | 10.50 | 26.25 |
| Sodium cocoyl isethionate | 49.50 | 123.75 |

Comments: Penetration = 40; Si/PJ = 0.26; foams well.

| EXAMPLE 43 | | |
|---|---|---|
| Petroleum Jelly | 40.00 | 100.00 |
| Fumed Silica | 13.00 | 32.50 |
| Sodium cocoyl isethionate | 47.00 | 117.50 |

Comments: Penetration = 35; Si/PJ = 0.325; foams well.

| EXAMPLE 44 | | |
|---|---|---|
| Petroleum Jelly | 30.00 | 75.00 |
| Fumed Silica | 6.00 | 15.00 |
| Sodium cocoyl isethionate | 64.00 | 160.00 |

Comments: Penetration = 35; Si/PJ = 0.2; foams well.

| EXAMPLE 45 | | |
|---|---|---|
| Petroleum Jelly | 30.00 | 75.00 |
| Fumed Silica | 8.00 | 20.00 |
| Sodium cocoyl isethionate | 62.00 | 155.00 |

Comments: Penetration = 30; Si/PJ = 0.267; foams well.

| EXAMPLE 46 | | |
|---|---|---|
| Petroleum Jelly | 30.00 | 75.00 |
| Fumed Silica | 10.00 | 25.00 |
| Sodium cocoyl isethionate | 60.00 | 150.00 |

Comments: Penetration = 23; Si/PJ = 0.33; foams well.

| EXAMPLE 47 | | |
|---|---|---|
| Petroleum Jelly | 20.00 | 50.00 |
| Fumed Silica | 4.00 | 10.00 |
| Sodium cocoyl isethionate | 76.00 | 190.00 |

Comments: Penetration = 25; Si/PJ = 0.2; good foam.

| EXAMPLE 48 | | |
|---|---|---|
| Petroleum Jelly | 20.00 | 50.00 |
| Fumed Silica | 5.50 | 13.75 |
| Sodium cocoyl isethionate | 74.50 | 186.25 |

Comments: Penetration = 17; Si/PJ = 0.275; foams well.

| EXAMPLE 49 | | |
|---|---|---|
| Petroleum Jelly | 20.00 | 50.00 |
| Fumed silica | 6.50 | 16.25 |
| Sodium cocoyl isethionate | 73.50 | 183.75 |

Comments: Penetration = 15; Si/PJ = 0.325; foams well.

| EXAMPLE 50 | | |
|---|---|---|
| Petroleum Jelly | 40.00 | 100.00 |
| Fumed Silica | 8.00 | 20.00 |
| Disodium Lauryl Sulfosuccinate | 52.00 | 130.00 |

Comments: Penetration = 45; Si/PJ = 0.2; foams well. The disodium lauryl sulfosuccinate used in this and other Examples is available under the designation Monamate LA-100 from Mona Industries, Patterson, N.J.

| EXAMPLE 51 | | |
|---|---|---|
| Petroleum Jelly | 40.00 | 100.00 |
| Fumed Silica | 10.50 | 26.25 |
| Disodium Lauryl Sulfosuccinate | 49.50 | 123.75 |

Comments: Penetration = 35; Si/PJ = 0.26; foams well.

| EXAMPLE 52 | | |
|---|---|---|
| Petroleum Jelly | 40.00 | 100.00 |
| Fumed Silica | 13.00 | 32.50 |
| Disodium Lauryl Sulfosuccinate | 47.00 | 117.50 |

Comments: Penetration = 25; Si/PJ = 0.325; foams well.

| EXAMPLE 53 | | |
|---|---|---|
| Petroleum Jelly | 30.00 | 75.00 |
| Fumed Silica | 6.00 | 15.00 |
| Disodium Lauryl Sulfosuccinate | 64.00 | 160.00 |

Comments: Penetration = 30; Si/PJ = 0.2; foams well.

| EXAMPLE 54 | | |
|---|---|---|
| Petroleum Jelly | 30.00 | 75.00 |
| Fumed Silica | 8.00 | 20.00 |
| Disodium Lauryl Sulfosuccinate | 62.00 | 155.00 |

Comments: Penetration = 22; Si/PJ = 0.27; foams well.

| EXAMPLE 55 | | |
|---|---|---|
| Petroleum Jelly | 30.00 | 75.00 |
| Fumed Silica | 10.00 | 25.00 |
| Disodium Lauryl | 60.00 | 150.00 |

-continued

| | | |
|---|---|---|
| Sulfosuccinate | | |
| Comments: Penetration = 15; Si/PJ = 0.33; foams well. | | |

EXAMPLE 56

| | | |
|---|---|---|
| Petroleum Jelly | 20.00 | 50.00 |
| Fumed Silica | 4.00 | 10.00 |
| Disodium Lauryl Sulfosuccinate | 76.00 | 190.00 |
| Comments: Penetration = 20; Si/PJ = 0.2; foams well. | | |

EXAMPLE 57

| | | |
|---|---|---|
| Petroleum Jelly | 20.00 | 50.00 |
| Fumed Silica | 6.50 | 16.25 |
| Disodium Lauryl Sulfosuccinate | 73.50 | 183.75 |
| Comments: Penetration = 14; Si/PJ = 0.325; foams well. | | |

EXAMPLE 58

| | | |
|---|---|---|
| Petroleum Jelly | 20.00 | 50.00 |
| Fumed Silica | 5.50 | 13.75 |
| Disodium Lauryl Sulfosuccinate | 74.50 | 186.25 |
| Comments: Penetration = 18; Si/PJ = 0.275; foams well. | | |

EXAMPLE 59

| | | |
|---|---|---|
| Petroleum Jelly | 30.00 | 75.00 |
| Fumed Silica | 8.00 | 20.00 |
| Sodium cocoyl isethionate | 31.00 | 77.50 |
| Disodium Lauryl Sulfosuccinate LA-100 | 31.00 | 77.50 |
| Comments: Penetration = 35; Si/PJ = 0.27; foaming characteristics good. | | |

EXAMPLE 60

| | | |
|---|---|---|
| Petroleum Jelly | 40.00 | 100.00 |
| Fumed Silica | 8.00 | 20.00 |
| Sodium cocoyl isethionate | 26.00 | 65.00 |
| Disodium Lauryl Sulfosuccinate | 26.00 | 65.00 |
| Comments: Penetration = 52; Si/PJ = 0.2; very good foaming characteristics. | | |

EXAMPLE 61

| | | |
|---|---|---|
| Petroleum Jelly | 40.00 | 100.00 |
| Fumed Silica | 8.00 | 26.25 |
| Sodium cocoyl isethionate | 24.75 | 61.90 |
| Disodium Lauryl Sulfosuccinate | 24.75 | 61.90 |
| Comments: Penetration = 42; Si/PJ = 0.2625; very good foaming characteristics. | | |

EXAMPLE 62

| | | |
|---|---|---|
| Petroleum Jelly | 40.00 | 100.00 |
| Fumed Silica | 13.00 | 32.50 |
| Sodium cocoyl isethionate | 23.50 | 58.75 |
| Disodium Lauryl Sulfosuccinate | 23.50 | 58.75 |
| Comments: Penetration = 30; Si/PJ = 0.325; very good foaming characteristics. | | |

EXAMPLE 63

| | | |
|---|---|---|
| Petroleum Jelly | 30.00 | 75.00 |
| Fumed Silica | 6.00 | 15.00 |
| Sodium cocoyl isethionate | 32.00 | 80.00 |
| Disodium Lauryl Sulfosuccinate | 32.00 | 80.00 |
| Comments: Penetration = 42; Si/PJ = 0.2; very good foaming characteristics. | | |

EXAMPLE 64

| | | |
|---|---|---|
| Petroleum Jelly | 30.00 | 75.00 |
| Fumed Silica | 10.00 | 25.00 |
| Sodium cocoyl isethionate | 30.00 | 75.00 |

-continued

| | | |
|---|---|---|
| Disodium Lauryl Sulfosuccinate | 30.00 | 75.00 |
| Comments: Penetration = 27; Si/PJ = 0.33; very good foaming characteristics. | | |

EXAMPLE 65

| | | |
|---|---|---|
| Petroleum Jelly | 20.00 | 50.00 |
| Fumed Silica | 4.00 | 10.00 |
| Sodium cocoyl isethionate | 38.00 | 95.00 |
| Disodium Lauryl Sulfosuccinate | 38.00 | 95.00 |
| Comments: Penetration = 26; Si/PJ = 0.2; very good foaming characteristics. | | |

EXAMPLE 66

| | | |
|---|---|---|
| Petroleum Jelly | 20.00 | 50.00 |
| Fumed Silica | 5.50 | 13.75 |
| Sodium cocoyl isethionate | 37.50 | 93.75 |
| Disodium Lauryl Sulfosuccinate | 37.00 | 92.50 |
| Comments: Penetration = 20; Si/PJ = 0.275; very good foaming characteristics. | | |

EXAMPLE 67

| | | |
|---|---|---|
| Petroleum Jelly | 20.00 | 50.00 |
| Fumed Silica | 6.50 | 13.25 |
| Sodium cocoyl isethionate | 37.00 | 92.50 |
| Disodium Lauryl Sulfosuccinate | 36.50 | 91.50 |
| Comments: Penetration = 17; Si/PJ = 0.375; very good foaming characteristics. | | |

EXAMPLE 68

| | | |
|---|---|---|
| Petroleum Jelly | 20.00 | 50.00 |
| Fumed Silica | 4.00 | 10.00 |
| Sodium $C_{14-16}$ Olefin Sulfonate | 76.00 | 190.00 |
| Comments: Penetration = 34; Si/PJ = 0.2; foams well. | | |

EXAMPLE 69

| | | |
|---|---|---|
| Petroleum Jelly | 20.00 | 50.00 |
| Fumed Silica | 5.50 | 13.75 |
| Sodium $C_{14-16}$ Olefin Sulfonate | 74.50 | 186.25 |
| Comments: Penetration = 25; Si/PJ = 0.275; foams well. | | |

EXAMPLE 70

| | | |
|---|---|---|
| Petroleum Jelly | 20.00 | 50.00 |
| Fumed Silica | 6.50 | 16.25 |
| Sodium $C_{14-16}$ Olefin Sulfonate | 73.50 | 183.75 |
| Comments: Penetration = 21; Si/PJ = 0.325; good foam. | | |

EXAMPLE 71

| | | |
|---|---|---|
| Petroleum Jelly | 30.00 | 75.00 |
| Fumed silica | 6.00 | 15.00 |
| Sodium $C_{14-16}$ Olefin Sulfonate | 64.00 | 160.00 |
| Comments: Penetration = 47; Si/PJ = 0.2; good foam. | | |

EXAMPLE 72

| | | |
|---|---|---|
| Petroleum Jelly | 30.00 | 75.00 |
| Fumed silica | 8.00 | 20.00 |
| Sodium $C_{14-16}$ Olefin Sulfonate | 62.00 | 155.00 |
| Comments: Penetration = 25; Si/PJ = 0.267; good foam. | | |

EXAMPLE 73

| | | |
|---|---|---|
| Petroleum Jelly | 30.00 | 75.00 |
| Fumed silica | 10.00 | 25.00 |
| Sodium $C_{14-16}$ Olefin Sulfonate | 60.00 | 150.00 |
| Comments: Penetration = 22; Si/PJ = 0.33; good foam. | | |

EXAMPLE 74

| | | |
|---|---|---|
| Petroleum Jelly | 40.00 | 100.00 |
| Fumed silica | 8.00 | 20.00 |
| Sodium C$_{14-16}$ Olefin Sulfonate | 52.00 | 130.00 |

Comments: Penetration = 48; Si/PJ = 0.2; good foam.

EXAMPLE 75

| | | |
|---|---|---|
| Petroleum Jelly | 40.00 | 100.00 |
| Fumed silica | 10.50 | 26.25 |
| Sodium C$_{14-16}$ Olefin Sulfonate | 49.50 | 123.75 |

Comments: Penetration = 32; Si/PJ = 0.2625; good foam.

EXAMPLE 76

| | | |
|---|---|---|
| Petroleum Jelly | 40.00 | 100.00 |
| Fumed silica | 13.00 | 32.50 |
| Sodium C$_{14-16}$ Olefin Sulfonate | 49.50 | 123.75 |

Comments: Penetration = 25; Si/PJ = 0.325; good foam.

| | % | 500 g |
|---|---|---|

EXAMPLE 77

| | | |
|---|---|---|
| Petroleum Jelly | 30.00 | 150.00 |
| Fumed silica | 8.00 | 40.00 |
| Sodium cocoyl isethionate | 15.00 | 75.00 |
| Disodium Lauryl Sulfosuccinate | 15.00 | 75.00 |
| Potassium Polymetaphosphate | .40 | 2.00 |
| Corn Starch | 15.80 | 79.00 |
| Soap base | 15.80 | 79.00 |

Comments: Penetration = 25; Si/PJ = 0.267; good foam. See Table II for Composition of soap base.

EXAMPLE 78

| | | |
|---|---|---|
| Petroleum Jelly | 30.00 | 150.00 |
| Fumed silica | 8.00 | 40.00 |
| Sodium cocoyl isethionate | 15.00 | 75.00 |
| Disodium lauryl sulfosuccinate | 15.00 | 75.00 |
| Potassium polymetaphosphate | 0.4 | 2.00 |
| Soap base | 31.60 | 158.00 |

Comments: Penetration = 42; Si/PJ = 0.267; sticky, soft.

EXAMPLE 79

| | | |
|---|---|---|
| Petroleum Jelly | 30.00 | 150.00 |
| Fumed silica | 8.00 | 40.00 |
| Sodium cocoyl isethionate | 15.00 | 75.00 |
| Disodium lauryl sulfosuccinate | 15.00 | 75.00 |
| Potassium polymetaphosphate | .40 | 2.00 |
| Syndet/Soap base | 31.60 | 158.00 |

Comments: Penetration = 40; Si/PJ = 0.267; too tacky, sticky. See Table III for formulation of syndet/soap base.

| | % | 250 g |
|---|---|---|

EXAMPLE 80

| | | |
|---|---|---|
| Petroleum Jelly | 30.00 | 75.00 |
| Fumed silica | 8.00 | 20.00 |
| Sodium cocoyl isethionate | 15.00 | 37.50 |
| Disodium lauryl sulfosuccinate | 15.00 | 37.50 |
| Potassium polymetaphosphate | .40 | 1.00 |
| Confectioners' sugar | 15.80 | 39.50 |
| Soap base | 15.80 | 39.50 |

Comments: Penetration = 36; Si/PJ = 0.267; See Table II for composition of soap base.

EXAMPLE 81

| | | |
|---|---|---|
| Petroleum Jelly | 30.00 | 75.00 |
| Fumed silica | 8.00 | 20.00 |
| Sodium cocoyl isethionate | 15.00 | 37.50 |
| Disodium lauryl sulfosuccinate | 32.00 | 80.00 |
| Soap base | 15.00 | 37.50 |

Comments: Penetration = 40; Si/PJ = 0.267; good foaming characteristics. See Table II for composition of soap base.

EXAMPLE 82

| | | |
|---|---|---|
| Avocado Oil | 30.00 | 75.00 |
| Fumed silica | 8.00 | 20.00 |
| Sodium cocoyl isethionate | 62.00 | 155.00 |

Comments: Penetration = 24; Si/Oil = 0.267; foams very well.

EXAMPLE 83

| | | |
|---|---|---|
| Sesame Oil | 30.00 | 75.00 |
| Fumed silica | 8.00 | 20.00 |
| Sodium cocoyl isethionate | 62.00 | 155.00 |

Comments: Penetration = 24; Si/Oil = 0.267; foams very well, but tacky.

EXAMPLE 84

| | | |
|---|---|---|
| Mineral Oil | 30.00 | 75.00 |
| Fumed silica | 8.00 | 20.00 |
| Sodium cocoyl isethionate | 62.00 | 155.00 |

Comments: Si/Oil = 0.267; Foams well.

EXAMPLE 85

| | | |
|---|---|---|
| Polydecene | 30.00 | 75.00 |
| Fumed silica | 8.00 | 20.00 |
| Sodium cocoyl isethionate | 62.00 | 155.00 |

Comments: Si/Oil = 0.267; Foams well.

EXAMPLE 86

| | | |
|---|---|---|
| Petroleum Jelly | 30.00 | 75.00 |
| Fumed silica | 8.00 | 20.00 |
| Sodium cocoyl isethionate | 57.00 | 142.50 |
| C$_{12-15}$ Alkyl Benzoate | 5.0 | 12.50 |

Comments: Si/PJ = 0.267; the C$_{12-15}$ Alkyl Benzoate used in this and other Examples is available under the designation FIN-SOLV-TN from Finetex, Inc., Elmwood Park, NJ.

EXAMPLE 87

| | | |
|---|---|---|
| Petroleum Jelly | 20.00 | 50.00 |
| Fumed silica | 8.00 | 20.00 |
| Sodium cocoyl isethionate | 57.00 | 142.50 |
| C$_{12-15}$ Alkyl Benzoate | 5.0 | 12.50 |
| Benzoyl Peroxide | 10.0 | 25.00 |

Comments: Si/PJ = 0.267.

EXAMPLE 88

| | | |
|---|---|---|
| Petroleum Jelly | 20.00 | 50.00 |
| Fumed silica | 8.00 | 20.00 |
| Sodium cocoyl isethionate | 57.00 | 142.50 |
| Triclosan | .5 | 1.25 |

Comments: Si/PJ = 0.267.

While the above description contains many specific details of compositions and has in accordance with this invention, these specific details should not be construed as limitations on the scope of the invention, but merely as exemplifications of preferred embodiments thereof. Those skilled in the art will envision many other possible variations that all within the scope and spirit of the invention as defined by the claims appended hereto.

We claim:

1. A method of preparing a cleansing bar comprising:

adding particulate silica having a surface area of at least 75 $m^2/gm$ to an oil phase containing oil and optionally wax to provide a mixture comprising oil and silica;

combining the mixture with a cleansing agent comprising one or more synthetic detergents to provide a cleansing composition having a penetration value of about 50 or less; and forming the cleansing composition into a bar.

2. A method as in claim 1 wherein the particulate silica is added to the oil phase at weight ratio of about 1:2 to about 1:7.

3. A method as in claim 1 wherein fumed silica is added to petroleum jelly to form a mixture.

4. A method as in claim 1 wherein the cleansing agent combined with the mixture comprises a synthetic detergent selected from the group consisting of sodium acyl isothionates, sodium alpha olefin sulfonates and disodium alkyl sulfosuccinates.

5. A method of preparing a cleansing bar comprising:

adding fumed silica having a surface area of at least 75 $m^2/gm$ to an oil phase containing petroleum jelly and optionally wax to provide a mixture;

combining the mixture with a cleansing agent selected from the group consisting of soaps, synthetic detergents and combinations thereof to provide a cleansing composition having a penetration value of about 50 or less; and forming the cleansing composition into a bar.

6. A method of preparing a cleansing bar comprising:

adding particulate silica having a surface area of at least 75 $m^2/gm$ to an oil phase containing oil and optionally wax to provide a mixture;

combining the mixture with a synthetic detergent selected from the group consisting of sodium acyl isethionates, sodium alpha olefin sulfonates and disodium alkyl sulfosuccinates to provide a cleansing composition having a penetration value of about 50 or less; and forming the cleansing composition into a bar.

* * * * *